(12) United States Patent
Thakkar

(10) Patent No.: US 8,734,448 B2
(45) Date of Patent: May 27, 2014

(54) IMPLANT ASSEMBLY FOR PROXIMAL FEMORAL FRACTURE

(76) Inventor: Navin N Thakkar, Ahmedabad (IN)

( * ) Notice: Subject to any disclaimer, the term of this patent is extended or adjusted under 35 U.S.C. 154(b) by 1044 days.

(21) Appl. No.: 10/599,855

(22) PCT Filed: Apr. 7, 2005

(86) PCT No.: PCT/IN2005/000102
§ 371 (c)(1),
(2), (4) Date: Oct. 11, 2006

(87) PCT Pub. No.: WO2005/096977
PCT Pub. Date: Oct. 20, 2005

(65) Prior Publication Data
US 2007/0219636 A1    Sep. 20, 2007

(30) Foreign Application Priority Data
Apr. 12, 2004    (IN) .......................... 437/MUM/2004

(51) Int. Cl.
*A61B 17/58*    (2006.01)
(52) U.S. Cl.
USPC .................................. 606/64; 606/62; 606/68
(58) Field of Classification Search
USPC .............. 606/67, 62, 69, 70, 98, 63–66, 68, 606/280–299, 71; 623/18.11
See application file for complete search history.

(56) References Cited

U.S. PATENT DOCUMENTS

| 2,702,543 A | 2/1955 | Pugh et al. |
| 3,094,120 A | 6/1963 | Blosser |
| 3,374,786 A | 3/1968 | Callender, Jr. |
| 3,670,724 A * | 6/1972 | Bosacco .......................... 606/64 |
| 3,842,825 A | 10/1974 | Wagner |
| 3,892,233 A * | 7/1975 | Vestby ............................ 606/67 |
| 4,432,358 A | 2/1984 | Pixel |
| 4,475,545 A | 10/1984 | Ender |
| 4,530,355 A | 7/1985 | Griggs |

(Continued)

FOREIGN PATENT DOCUMENTS

| EP | 0496950 | 8/1992 |
| EP | 0617927 | 10/1994 |

(Continued)

OTHER PUBLICATIONS http://www.thefreedictionary.com/unitary, Definition for unitary, accessed on Feb. 4, 2010.*

(Continued)

*Primary Examiner* — Jan Christopher Merene

(57) ABSTRACT

An implant assembly for proximal femur fracture comprises of a targeting device and intramedullary nail having plurality of proximal holes directed towards head and neck of femur wherein the axis of the holes makes an ante version angle of about 5° to 20° with the horizontal plane and at the same time axis of plurality of distal holes making 90° angle to longitudinal axis of said nail that holds the femur wherein said nail has reducing cross section area from thigh end to knee end with grooved knee end with anterior curvature even in short length version, plurality of proximal sliding hip pins with smooth shaft for collapsibility, triflanged end with mores taper to hold proximal femur, large head and washer to get impaction and plurality of distal locking screw to hold distal fragment of femur, optional buttress plate and barrels supporting lateral cortex to get controlled limited guided collapse.

18 Claims, 19 Drawing Sheets

(56) References Cited

U.S. PATENT DOCUMENTS

| | | | |
|---|---|---|---|
| 4,733,654 A * | 3/1988 | Marino | 606/64 |
| 4,805,607 A * | 2/1989 | Engelhardt et al. | 606/67 |
| 4,827,917 A | 5/1989 | Brumfield | |
| 5,032,125 A | 7/1991 | Durham et al. | |
| 5,035,697 A * | 7/1991 | Frigg | 606/67 |
| 5,041,115 A * | 8/1991 | Frigg et al. | 606/62 |
| 5,122,141 A | 6/1992 | Simpson et al. | |
| 5,334,192 A * | 8/1994 | Behrens | 606/96 |
| 5,462,547 A * | 10/1995 | Weigum | 606/65 |
| 5,549,612 A * | 8/1996 | Yapp et al. | 606/69 |
| 5,562,666 A | 10/1996 | Brumfield | |
| 5,591,168 A * | 1/1997 | Judet et al. | 606/65 |
| 5,697,930 A * | 12/1997 | Itoman et al. | 606/62 |
| 5,728,128 A * | 3/1998 | Crickenberger et al. | 606/97 |
| 5,766,174 A * | 6/1998 | Perry | 606/62 |
| 5,810,821 A * | 9/1998 | Vandewalle | 606/65 |
| 5,908,422 A * | 6/1999 | Bresina | 606/67 |
| 5,935,127 A * | 8/1999 | Border | 606/62 |
| 5,951,557 A * | 9/1999 | Luter | 606/69 |
| 6,039,739 A * | 3/2000 | Simon | 606/64 |
| 6,096,040 A * | 8/2000 | Esser | 606/69 |
| 6,106,528 A * | 8/2000 | Durham et al. | 606/64 |
| 6,123,708 A * | 9/2000 | Kilpela et al. | 606/62 |
| 6,187,007 B1 * | 2/2001 | Frigg et al. | 606/72 |
| 6,214,012 B1 * | 4/2001 | Karpman et al. | 606/93 |
| 6,623,486 B1 * | 9/2003 | Weaver et al. | 606/69 |
| 6,702,823 B2 * | 3/2004 | Iaia | 606/98 |
| 6,932,818 B2 * | 8/2005 | Behrens | 606/64 |
| 2002/0032445 A1 * | 3/2002 | Fujiwara | 606/67 |
| 2002/0058949 A1 * | 5/2002 | Iaia | 606/98 |
| 2002/0099379 A1 * | 7/2002 | Adam | 606/67 |
| 2002/0151897 A1 * | 10/2002 | Zirkle, Jr. | 606/62 |
| 2003/0073999 A1 * | 4/2003 | Putnam | 606/62 |
| 2003/0083662 A1 * | 5/2003 | Middleton | 606/72 |

FOREIGN PATENT DOCUMENTS

| | | |
|---|---|---|
| EP | 1273271 | 1/2003 |
| EP | 1329197 | 7/2003 |
| FR | 2717674 | 9/1995 |
| WO | PCT/CH/99/00581 | 7/2001 |

OTHER PUBLICATIONS

International Search Report for PCT/IN2005/000102, Published by ISA/EP; Dated Sep. 12, 2005. (pp. 1-4).
By Richard F. Kyle, M.D.F. Minneapolis, Minnesota, "Fractures of thee Proximal Part of the Femur"; 4524 The Journal of Bone and Joint Surgery vol. 76A Jun. 1994, No. 6, Boston, MA, US., pp. 1-24.

* cited by examiner

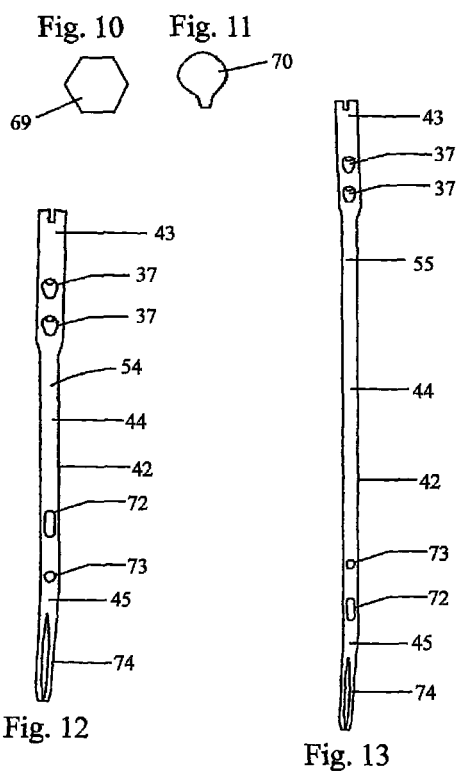

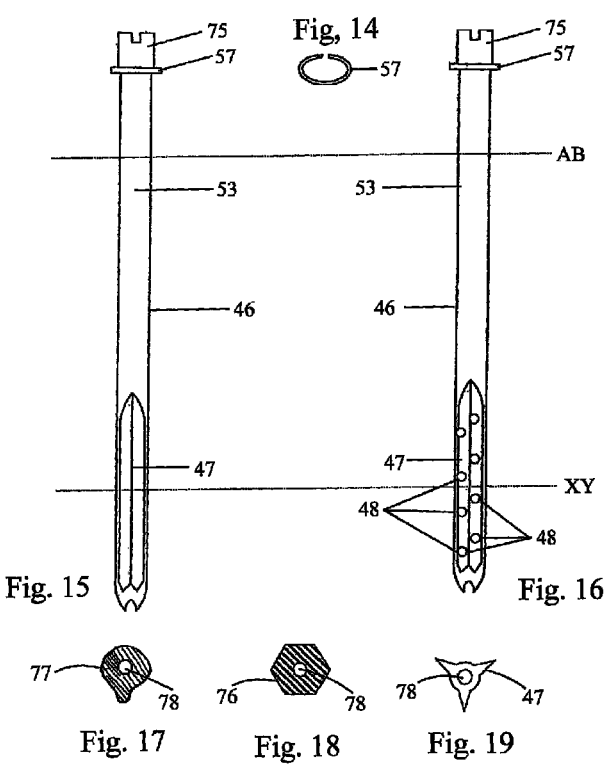

IMPLANT ASSEMBLY FOR PROXIMAL FEMORAL FRACTURE

The present application is related to and claims priority from PCT application PCT/IN2005/000102 filed on 7 Apr. 2005, which in turn claims priority from India Patent Application 437/MUM/2004 filed on 12 Apr. 2004, which are both incorporated in their entirety herewith.

TECHNICAL FIELD

The present invention relates to an implant assembly used to repair fractures of the Proximal Femur and ipsilateral (same side) fractures of shaft of femur by one piece (unitary) intramedullary nail having complete anatomical profile like femur bone and its minimally invasive method for insertion by using targeting device with it.

BACKGROUND ART

The femur bone (thigh bone) has peculiar shape and curvatures (anatomical profile) comprising of its Head (1), Neck (2), Greater Trochanter (3), Lesser trochanter (4) and Shaft (5). Head portion is like a ball composed of dense cancellous bone. Neck has front (anterior) surface (6), back (posterior) surface (7), lower (inferior) surface (8) and upper (superior) surface (9). Neck is not cylindrical in cut section but flat and narrow near posterior and inferior surface having dense good quality bone called as calcar (10) and broad at superior portion containing less dense bone near superior and anterior surface. Axis of centre of shaft (11) makes an angle with axis of centre of neck and head (12) which is known as "neck shaft angle" (13), which generally varies from 120° to 140°. Plane of center of shaft of femur (14) makes an angle with the plane of center of neck and head (15), which is known as "angle of ante version" (16), and which generally varies from 5° to 20°. Hollow shaft of femur with medullary canal (17) has "anterior curvature" (18). Front wall of medullary canal of shaft of femur is called anterior cortex (19), back wall is called posterior cortex (20), inner wall is called medial cortex (21) and outer wall is called lateral cortex (22). Head (1) articulates with socket-acetabulum (23) making the hip joint. Portion of femur bone comprising head (1), neck (2) and upper part of shaft(5) is called as "Proximal Femur". In normal human, various muscles are attached to this part of bone, exerting force and reacting to ground reaction force in different directions and in different amplitudes in different stages of walking, and these loads are cyclic in nature. In intact femur bone these forces are transmitted from proximal femur to shaft of femur effectively.

Incidences of unstable proximal femur fractures in elderly people are very high world wide and management of these geriatric or aged patients has become a challenge. These geriatric patients with old age osteoporosis require early mobilization with assisted full weight bearing. In this situation it is essential that different forces acting on the femur should be transferred efficiently to the fracture fragments without displacement, leading to healing of fracture.

This demands implant assembly with proper biomechanical properties, such as:

- The implant should acquire minimum area of the bone to provide anatomical reconstruction with stable biological (MINIMALLY INVASIVE) osteosynthesis (fixation of fractured bone fragments).
- The funnel shaped femur medullary canal (17) makes an ante version angle (16) of around 5° to 20° with neck and head of femur bone and the femur shaft has anterior curvature (18). The implant must match completely with the above mentioned anatomic profile of femur bone to distribute the forces evenly like an intact bone.
- At the same time implant should be capable to react effectively to large, dynamic (in magnitude and direction) and cyclic loads when patient starts walking bearing the weight on limb. Implant should allow gradual adaptation of the fractured bone fragments by allowing guided limited controlled collapse of gap between the fixed bone fragments leading to early bone to bone contact which results into faster healing.
- Implant should be stable enough to provide rotational stability, so that during any rotational forces the implant and the comminuted bone should move as one unit.
- Implant design and fixation must be such that it should provide early mobilization and should allow assisted full weight bearing.
- The femur size and other related properties vary from person to person. Therefore, it is necessary to develop an implant assembly that would be suitable for any femur which meets the essential parameters. Along with these biomechanical properties, the implant unit should be easy to fix and should provide maximum accuracy of fixation, so that it is adoptable to average surgeon giving reproducible results.

There are a variety of devices used to treat proximal femoral fractures. Fractures of the neck, head or intertrochanter of the femur have been successfully treated with a variety of Dynamic Hip Screw (DHS) assemblies as shown in FIG. 4, which generally include a compression plate (24) with a barrel member (25), a lag screw (26) and a compressing screw (27). The compression plate (24) is secured to the exterior of the femur-lateral cortex (22) and the barrel member (25) is inserted into a predrilled hole in the direction of the femoral head (1). The lag screw (26), which has a threaded end (28) and a smooth portion (29), is inserted through the barrel member (25), so that it extends across the break and into the femoral head. The threaded portion (28) engages the femoral head. The compressing screw (27) connects the lag screw (26) to the plate (24). By adjusting the tension of the compressing screw (27), the compression (reduction) of the fracture can be adjusted. The smooth portion (29) of the lag screw must be free to slide through the barrel member (25) to permit the adjustment of the compression screw. Compression screw assemblies are shown by the following patents: Pixel U.S. Pat. No. 4,432,358; Callender, Jr. U.S. Pat. No. 3,374,786; Pugh et al. U.S. Pat. No. 2,702,543; Griggs U.S. Pat. No. 4,530,355; Blosser, U.S. Pat. No. 3,094,120; and Wagner U.S. Pat. No. 3,842,825. The Blosser and Wagner patents illustrate the use of multiple screws to prevent rotation of the lag screw relative to the compression plate and barrel member. A surgical bone pin, which functions like a lag screw and compressing screw, but which doe's not include a compression plate is shown by Cochran et al. U.S. Pat. No. 3,103,926. These assemblies fail in unstable fractures due to various biomechanical problems.

Subtrochanteric and femoral shaft fractures have been treated with the help of intramedullary rods which are inserted into the marrow canal of the femur to immobilize the femur parts involved in fractures. A single angled locking screw is inserted through the femur and the proximal end of the intramedullary rod. In some varieties, one or two screws may also be inserted through the femoral shaft and through the distal end of the intramedullary rod. The standard intramedullary rods have been successfully employed in treating fractures in lower portions of the femoral shaft.

The Grosse-Kempf nail, manufactured by Howmedica Company of Rutherford, N.J., is believed to be one of the earliest intramedullary nailing devices introduced into the United States. The Grosse-Kempf nail includes a threaded hole in the intramedullary rod for receiving the interlocking screw. The fully threaded screw cannot slide through the threaded hole to permit the type of compression found in the compression screw assemblies discussed above. Furthermore, the axis of the threaded hole coincides with a line between the greater to lesser trochanter and not in the direction of the femoral neck.

The commercially available Kuntscher Y-nail includes a flanged cloverleaf shaped intramedullary nail which is inserted through a hole in a single femoral neck nail. The rod includes a longitudinal slit. The Kuntscher device is indicated only for unstable trochanteric fractures. Neither the Kuntscher device, nor the Zickel nail, includes distal anchoring means and both therefore are not useful for treating distal fractures. The femoral neck nail of the Kuntscher device, which is angled toward the femoral neck, is locked into place by the intramedullary rod. Thus, the Kuntscher Y-nail is also not indicated for femoral neck fractures.

The Russell-Taylor interlocking nail system, manufactured by Richards Medical Company of Memphis, Tenn., includes an intramedullary rod having two pairs of coaxial holes through its proximal end. The axes of the pairs of holes intersect to provide a left or right orientation for insertion of a single locking screw. The screw is designed to pass from the greater to the lesser trochanter. There is not sufficient mechanical support to allow usage of the locking screw in the direction towards the femoral head because the second pair of coaxial holes weakens the nail when loaded in that direction. Further, the locking screw is a fully threaded screw which does not permit sliding of the screw relative to the intramedullary rod. Another bone-nail which permits left-right orientation by means of 'criss-cross' nail holes is shown by Ender U.S. Pat. No. 4,475,545.

Current intramedullary compression hip screw systems also provide new limitations that hamper their effectiveness. One such limitation is evident in both Lawes' and Durham's designs. These designs require the use of a set screw to prevent rotation of the lag screw; the set screw in the Lawes patent interacts directly with the lag screw, while Durham's is indirect with the lag screw. To ensure proper mating takes place the Smith & Nephew Richards' systems provides a torque wrench, while Howmedica's Gamma Nail system requires tightening of the set screw to full engagement and then backing it off. Over time, loss of calibration of the torque wrench and improper engagement by the surgeon user could lead to an unsatisfactory engagement and decreased usefulness.

As shown in FIG. 5, Howmedica's Gamma Nail system comprises of unitary Gamma Nail (30) with mediolateral angle and has a large proximal diameter (36) and single large hole (71) for a single large transfixing Gamma hip screw (31). Nail's distal end (32) is straight, of short length and pluralities of distal locking screws (33) are in same plane as of proximal hole (71) in nail.

Recently available Synthes -AO PFN, PCT/CH/99/00581 Application Number and WO 01 39679 A1 International Publication Number has described intramedullary nail has provision of plurality of transfixing hip screws, one large screw inferiorly near narrow calcar and one small screw superiorly. Proximal diameter of nail is large and direction of proximal holes and distal holes are in same plane in nail and targeting device. In short length nail, distal end is straight without any anterior curvature, so it is same for right or left side of femur.

Modular nailing systems have two piece nail, one base member and other extension member as disclosed by Simpson et al in U.S. Pat. No. 5,122,141, and other modular nails, taught in prior art, have modular sleeves or inserts, proved to be biomechanically improper and technically very difficult to implant in human body by surgeon.

Mechanical and clinical studies undertaken by inventor have revealed technical problems and disadvantages with prior art.

DISCLOSURE OF INVENTION

Technical Problems

1. Anatomical profile of femur is such that plane passing through centre of head and neck (15) makes an angle (16) with plane passing through the centre of shaft of femur (14). Unitary(non modular) intramedullary nails with targeting devices or jigs, taught in prior art, have proximal holes in nail and targeting device for proximal hip pins or screws to hold neck and head of femur bone and distal holes in nails and jig for distal interlocking screws to hold distal fragment of shaft of femur. These proximal holes and distal holes in nail and jig are in same plane without making any angle. This creates difficulty for surgeon in placement of proximal hip pins or screws in centre of head and neck of femur and distal locking screws in right direction, without rotating jig or limb of patient externally. Rotation of jig or targeting device leads to odd direction of distal interlocking screw and drilling in that direction may cause injury to the vital neurovascular structures, leading surgeon to abandon distal interlocking of nail. This leads to inadequate fixation or nonanatomic reconstruction of fractured proximal femur, having uneven force transmission to shaft of femur.

2. As shown in FIG. 6, Distal or knee end of short length intramedullary nails are straight, described in prior art, leading to stress concentration at tip of nail (34) abutting the anterior cortex (19) of femur bone, as shape of shaft of femur bone has anterior curvature(18). This "pointing effect" (35) gives rise to post operative thigh pain to patients, and stress concentration at this point leads to fracture of shaft of femur (5) beneath the nail later on.

3. Commercially available intramedullary nails providing plurality of proximal hip pins or screws have problem of superior "cut through" from neck of femur due to its more superior placement in neck of femur bone. This superior placement of screws or hip pins in neck occurs due to improper distance between two proximal holes in nail and targeting device and distance of holes from tip of proximal end of nail and large diameter of pin or screw. This happens particularly in group of patients having narrow femur neck leading to post operative pain and loss of anatomical reduction, also leading to shortening of limb and limp in gait.

4. Intramedullary nails of short length, taught in prior art, have same diameter and wall thickness through out the length of nail leading to high hoop stress while insertion, causing shattering of bone. This gives stress riser effect at distal or knee end and due to rigidity gives stress shielding at proximal or hip end leading to weakening of bone.

5. Intramedullary nails, taught in prior art, have larger diameter at proximal end (36) and corresponding proximal hip pins or screws also have larger diameter, requiring more reaming and removal of bone to accommodate intramedullary nail and hip screws leading to loss of more biological tissue which harms healing of fractured bone.

6. Design of proximal hip pins, taught in prior art, have screw tip with threads to hold head and neck part of femur bone, gives way under rotational forces when patient starts walking, particularly in unstable fracture pattern and osteoporotic bone, leading to loss of fixation.

7. Insertion of proximal hip screws, taught in prior art, requires rotatory movement leading to cutting of cancellous bone in head and neck part of femur leading to loose fixation, particularly in osteoporotic bone.

8. Proximal hip screws or pins, taught in similar devices in prior art, are not providing facility for augmentation of fixation in neck and head of femur bone by additional augmentation material like liquid inject-able bone cement or other material particularly in severely osteoporotic bone, where it is difficult to have sound fixation in head and neck of femur till repair of fracture.

9. Intramedullary nail devices with proximal hip screws or pins, taught in prior art, fails in situation where fracture pattern is such that there is void in lateral cortex (22) of femur bone or is badly weakened by fracture, these proximal hip screws or pins get pushed in inadvertently or it collapses too much with medial shift of shaft of femur on weight bearing postoperatively, hampering stability of fixation and leads to loss of fixation as there is nothing to support at lateral cortex (22) of femur, which is vital for controlled limited collapse of proximal fragment. This ultimately leads to shortening of limb and limp in gait of patient 10. Intramedullary devices with targeting device or jig, taught in prior art, have bulky jigs, which requires relatively larger incision and it obstructs viewing during fluoroscopy during surgery and thus increases blood loss and hampers precision during surgery. Jigs or targeting devices made out of radiolucent material are costly.

11. Short length intramedullary nails with targeting devices having facility to fix distal interlocking screw using targeting device to avoid fluoroscopic exposure to surgeon, taught in prior art, misses target of corresponding distal locking holes in the nail in patients where anterior curvature of femur(18) starts proximal to distal interlocking holes provided in nail and targeting device. It occurs also due to minor bending of straight short length nail inside medullary canal to partially adopt the shape of medullary canal.

12. Proximal holes in intramedullary nail acts as barrel, within which smooth sliding part of proximal sliding hip screws slides on weight bearing by patient. Shape of sliding part of proximal sliding hip screws and shape of proximal holes in intramedullary nails, taught in prior art, are round and do not give rotational stability in between these two parts of implant, leading to relatively uncontrolled sliding and collapse of fracture, giving rise to malunion of fracture.

Technical Solutions

1. Invention provides intramedullary nail (42) having direction of proximal holes of nails(37) and proximal holes in targeting device(38) in plane makes an angle of 5° to 20° (16) with plane passing through centre of shaft of femur (14) and the direction of distal locking holes of nail(39) and distal holes of targeting device(40) is at 90° to plane of centre of shaft of femur(14), so the direction of both proximal holes (37, 38) and both distal holes (39, 40) are in different planes matching anatomical profile of femur.

2. Invention provides intramedullary nail (42) having matching anterior curvature in distal or tail part of nail (45) even in short length version of nail (54), to match the anatomical anterior curvature of shaft of femur (18) avoiding abutting of nail tip (34) to anterior cortex (19), thus avoiding stress concentration.

3. Invention provides intramedullary nail (42), wherein distance from tip of proximal or head part of nail (43) to proximal holes in nail (37) and distance in between proximal holes in nail (37) is kept in such a way that it avoids superior "cut through" of neck(2) of femur by sliding proximal hip pins or screw (46). Same arrangement is given in targeting device (41).

4. Invention provides intramedullary nail (42) with gradually reducing diameter from proximal or head part (43) of nail to intermediate or shaft (44) part of nail to distal or tail (45) part of nail without any sudden change in diameter to match the funnel shape of intramedullary canal(17). Wall thickness of intramedullary nail is also reducing gradually from proximal to distal to match cortical thickness of femur bone.

5. Invention provides intramedullary nail having relatively smaller outer diameter of proximal or head portion (43) of intramedullary nail and smaller outer diameter of corresponding sliding proximal hip pins (46).

6. Invention provides design of sliding proximal hip pins (46) having triflange part (47) holding neck (2) and head (1) portion of femur. This "triflange" profile on cut section with more span and more taper provide good hold in neck and head part of femur and more rotational stability in unstable fracture pattern and osteoporotic bone. Other profiles like "U" or "Diamond" are also preferred.

7. Invention provides sliding proximal hip pins having "trifianged" part (47) or other profile and its method of insertion by gentle hammering on predrilled neck(2) and head(1) of femur leads to compaction of bone and minimal cutting of cancellous bone.

8. Invention provides proximal sliding hip pins (46) having small multiple holes (48) connecting central cannulation(78) in non sliding part of proximal hip pins(46) to inject augmentation material(49) like liquid bone cement through cannulated hip pins.

9. Invention provides buttress plate(50) cum washer with or without barrels(51) where sliding proximal hip pins(46) pass towards head and neck through central oblong holes(52) in buttress plate(50) providing buttress support to proximal fragment and lateral cortex(22), hence not allowing inadvertent push inside or uncontrolled collapse of sliding proximal hip pins(46). It also allows impaction of lateral fragment to fragment having head(1) and neck(2) part of femur, reducing the gap at fracture site.

10. Invention provides compact targeting device (41). Intramedullary nail (42) and sliding proximal hip pins (46) with cannulation providing guided precise insertion of implant.

11. Invention provides Intramedullary nail of short length version (54) with a targeting device(41) having corresponding distal locking holes in nail (39), and distal holes in targeting device (40) are at a distance, before start of anterior curvature(18) of shaft (5) of femur, so that it does not miss the target of holes in the nail.

12. Invention provides inner shape of proximal holes (37) in intramedullary nail (42) and outer shape of sliding part (53) of proximal hip pins (46) such that it gives rotation stability in between these two parts of implant allowing controlled, guided and limited sliding of proximal hip pins (46) on weight bearing by patient.

Advantageous Effects

1. This eliminates technical difficulty to surgeon of placing proximal sliding hip pins in centre of neck and head part of femur having good quality dense bone for better fixation and at the same time surgeon can pass distal interlocking screws in right direction without rotating the targeting device. It also maintains anatomical reduction, normal shape of femur and transmits forces acting on proximal femur bone evenly as if an intact normal bone.

2. Prevents postoperative thigh pain to patients and prevents future complication of fracture of shaft femur beneath the nail tip.

3. Prevents superior "cut through" of hip pins or screws, thus maintaining anatomical reduction of fractured fragments and prevents post operative pain to patient.

4. Prevents shattering of bone while insertion of intramedullary nail by surgeon and prevents stress rising at distal or knee end of nail and stress shielding and weakening of bone at proximal or hip end of nail.

5. Preserves more bone tissue by less removal of bone leading to early healing of fractured bone.

6. Preserves anatomical reduction even in unstable fracture pattern and osteoporotic bone of head and neck of femur.

7. Gives good rotational stability even in osteoporotic bone preventing loosening of fixation.

8. Allows augmentation of fixation, more stable fixation and hold in head and neck of femur preventing loosening of fixation in osteoporotic bone without hampering sliding mechanism.

9. Prevents complications of unnecessary push and penetration of sliding proximal hip pins(46) in hip joint leading to pain or uncontrolled collapse of sliding proximal hip pins (46), which in turn leads to loss of anatomical reduction and malunion of fracture. Gives additional support in unstable fracture pattern, allowing early rehabilitation of patient.

10. Smaller incision leads to less blood loss and less chances of infection, helps surgeon to insert implant guided with precision.

11. Provides precision in distal locking of short length version (54) of intramedullary nail (42) using targeting device (41) without harmful exposure of fluoroscopy to surgeon and patient during operation.

12. It provides limited, controlled guided collapse of fracture fragments maintaining anatomical reduction and union with normal shape of proximal femur.

DESCRIPTION OF DRAWINGS

FIG. 10 and show "hexagonal" shape of proximal holes in nail.

FIG. 11 shows "key hole" shape of proximal holes in nail.

FIGS. 12 and 13 show plan of short length version and full length version of intramedullary nail of invention respectively, FIG. 14 shows optional slit washer.

FIG. 15 shows elevation plan of sliding proximal hip pin.

FIG. 16 shows elevation plan of sliding proximal hip pin with multiple holes in nonsliding triflanged part.

FIG. 17 shows cut section of sliding part of proximal hip pin at line AB showing "key" shape with central hole for guide pin.

FIG. 18 shows cut section of sliding part of proximal hip pin at line AB showing "hexagonal" shape with central hole for guide pin.

FIG. 19 shows cut section of no sliding part of proximal hip pin at line XY showing "triflange" shape with central hole for guide pin.

MODE FOR INVENTION

Figure 1:
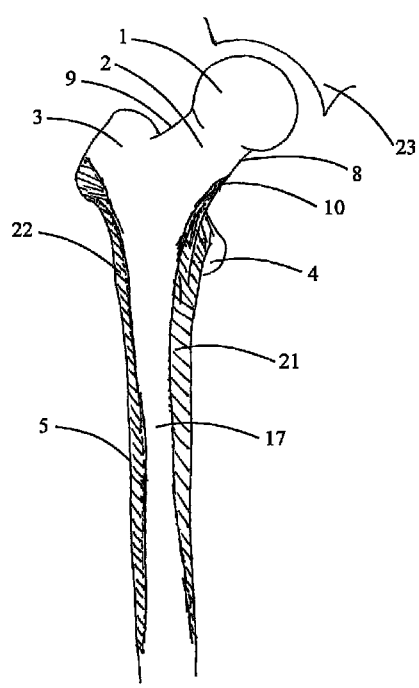
FIG. 1 shows front view of normal human femur showing different parts and surfaces.
Figure 2:
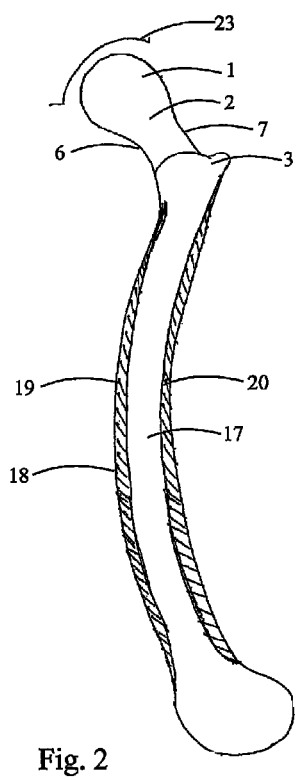
FIG. 2 shows side view of normal human femur showing different parts and surfaces.
Figure 3:
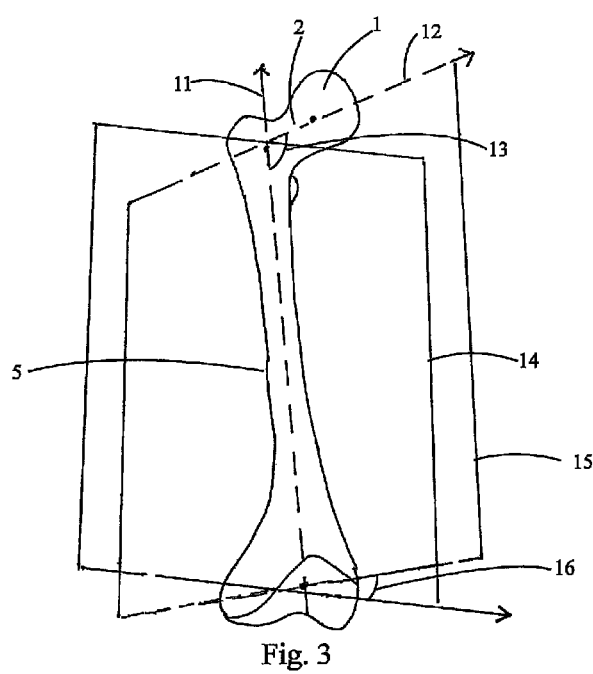
FIG. 3 shows normal angle of ante version and neck-shaft angle of femur.
Figure 4:
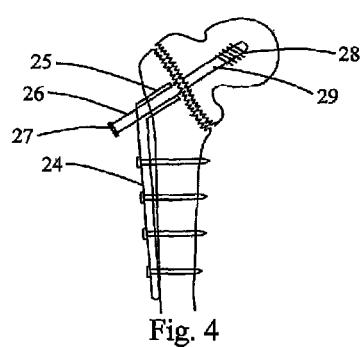
FIG. 4 shows schematic of Dynamic Hip Screw Implant implanted in proximal femur bone.

The invention is now described with the help of accompanying drawings as under:

The implant assembly mainly comprises of targeting device (41), intramedullary nail (42), proximal sliding hip pin (46), distal locking screw (56) and optional slitted buttress plate (50), slitted washer (57) and barrels (51).

Figure 8:
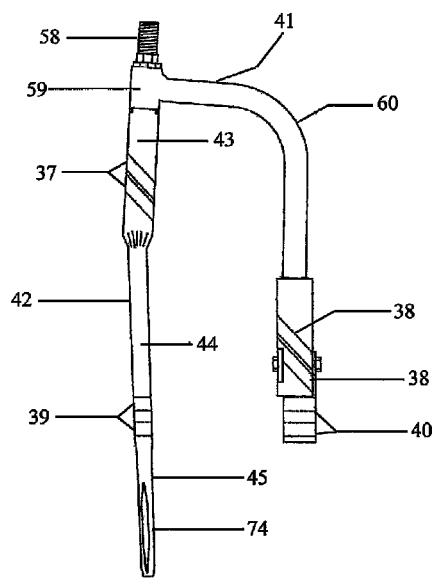
FIG. 8 shows side elevation of proposed implant showing targeting device with short length version nail mounted on targeting device.
Figure 9:
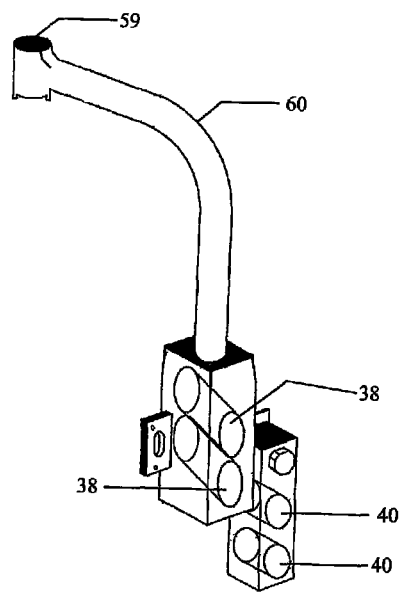
FIG. 9 shows isometric view of targeting device showing upper end, handle part, block of proximal holes and block of distal holes.
Figures 20, 21, 22, 23:
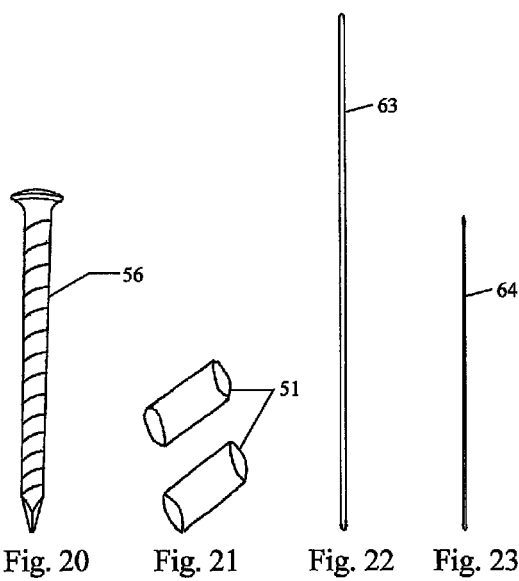
FIG. 20 shows elevation of distal interlocking screw.
FIG. 21 shows elevation of optional barrels.
FIG. 22 shows elevation of long blunt guide pin to guide intramedullary nail.
FIG. 23 shows elevation of short sharp guide pin to guide sliding proximal hip pin.
Figure 31:
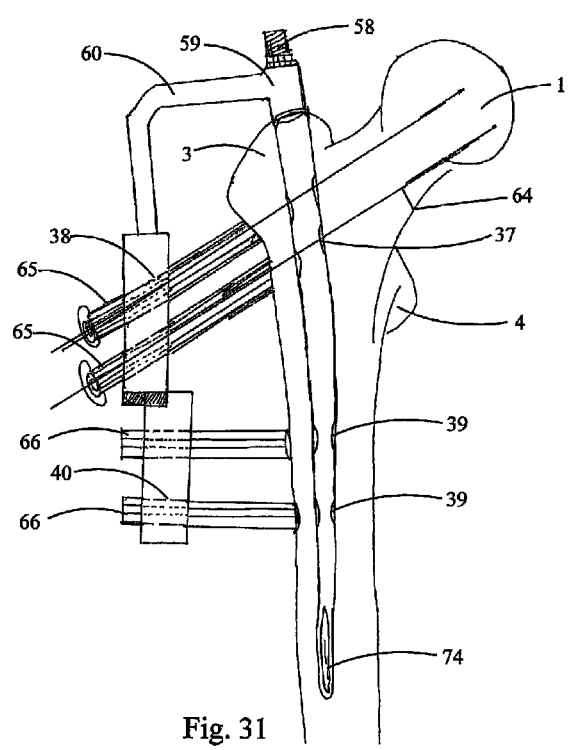
FIG. 31 shows implant assembly of present invention implanted in normal intact human femur showing short length version of intramedullary nail mounted on targeting device showing block of proximal holes of targeting device with tissue protection sleeves and guide pins for proximal sliding hip pins passing through sleeve in one plane and block of distal holes of targeting device with tissue protection sleeves targeting distal holes of intramedullary nail in another different plane.
Figure 32:
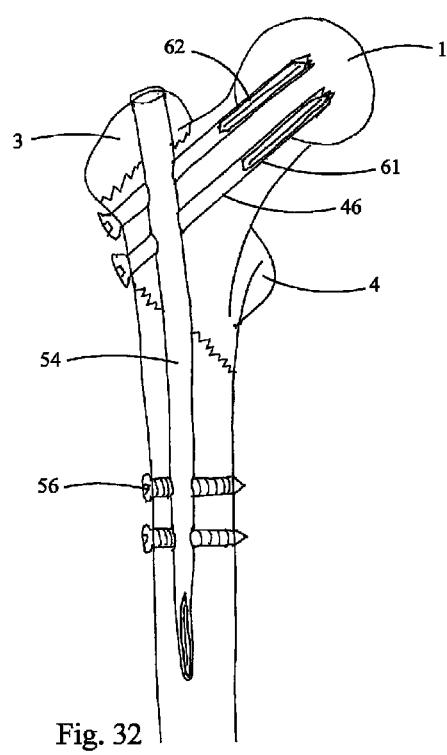
FIG. 32 shows implant assembly of present invention implanted in human femur with fractures for one example showing short length version of intramedullary nail, proximal sliding hip pins and distal interlocking screws.
Figure 33:
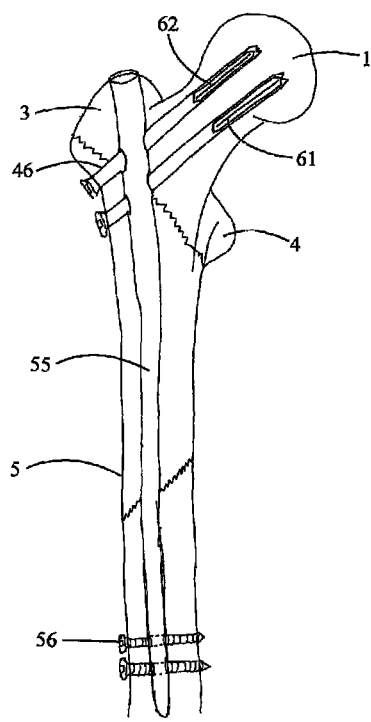
FIG. 33 shows implant assembly of present invention implanted in human femur having fracture in proximal femur and concomitant fracture in shaft of femur showing full length version of intramedullary nail, proximal sliding hip pins and distal interlocking screws.

Referring to FIG. 8, Targeting device (41) is connected to internally threaded part of thigh end portion or head (43) of Intramedullary nail (42) at compact cannulated connecting end (59) by short compact cannulated threaded connecting bolt (58), This makes targeting device compact, which helps to reduce the size of incision for insertion of nail reducing blood loss to patient and improved fluoroscopic viewing to surgeon during operation. This targeting device (41) can be made of non radiolucent material to get better strength and reduced cost. Referring to FIG. 9, targeting device (41) comprises of compact cannulated connecting end (59) at upper end, a handle part(60) for holding and manipulation during insertion of nail, block of plurality of parallel proximal holes (38) and block of plurality of distal holes (40) at lower end. To match with the anatomic profile of the femur, the axis of the proximal holes (38) of targeting device (41) makes an angle of about 120° to 140° to match neck shaft angle (13) of femur to target corresponding holes in intramedullary nail and at same time the plane of the proximal holes (38) of targeting device (41) makes an angle of about 5° to 20° with the horizontal plane to match ante version angle (16) of femur. This helps in placement of proximal hip pins in central part of neck and head of femur containing good quality dense bone for better hold and also helps to maintain normal shape of proximal femur. Axis of distal holes (40) of targeting device (41) makes 90° angle with central axis of shaft of femur (11). Block of plurality of proximal holes (38) of targeting device (41) and block of plurality of distal holes (40) are in different planes. Distance between tip of connecting end(59) of targeting device (41) and proximal holes of targeting device (38) is kept at "X" value, at same time distance in between proximal holes(38) of targeting device(41) is kept at "Y" value. The values of "X" and "Y" are kept in millimeters in such a way that placement of inferior sliding proximal hip pin (61) comes near calcar (10) which contains dense good quality of bone for better fixation and placement of superior proximal sliding hip pin (62) is avoided near superior surface of neck of femur (9) which contains relatively less dense bone. This avoids superior "cut through" of proximal sliding hip pins from neck and head. Distance between tip of connecting end (59) of targeting device (41) and distal holes (40) of targeting device (41) are kept of "Z" value. Value of "Z" is kept in millimeters such that distal holes (40) of targeting device (41) target distal corresponding holes (39) of nail before anterior curvature (18) of femur starts. This makes sure distal interlocking of screws through targeting device (41) in short length version of intramedullary nail (54) without any chance to miss the target due to anterior curvature (18) of shaft of femur. This helps surgeon to avoid harmful fluoroscopic radiation exposure. Block of plurality of proximal holes (38) of targeting device is used for both short length version of intramedullary nail (54) and full length version of intramedullary nail (55), while block of plurality of distal holes (40) of targeting device (41) is useful for short length version of intramedullary nails (54) only. FIG. 22 shows long blunt intramedullary guide pin (63) which is used to guide the intramedullary nail (42). FIG. 23 shows short sharp pointed guide pin (64) to guide cannulated "step drill bit" or "step reamer" for drilling in neck and head of femur and to guide proximal sliding hip pins (46) at final fixation. FIG. 31 shows set of three telescoping cannulated sleeves (65) of reducing diameter, first outer most larger diameter tissue protections sleeve, second intermediate telescoping drill sleeve to guide cannulated step drill bit or step reamer and third innermost with least diameter telescoping pin sleeve having cannulation to pass guide pin (64) towards direction of neck (2) and head (1), as known to person skilled in art. These sleeves are provided for block of proximal holes (38) of targeting device(41) to protect soft tissue, and have precise guided insertion of proximal sliding hip pins(41) through the corresponding proximal holes(37) of intramedullary nail(42). FIG. 31 shows set of two telescoping cannulated sleeves (66) of reducing diameter. First outer large diameter tissue protection sleeve is for tissue protection and telescoping second cannulated small diameter drill sleeve is for solid drill bit. These two sleeves are provided for block of distal plurality of holes (40) of targeting device (41) for tissue protection and for precise guided insertion of distal interlocking screws (56).

Figure 5:
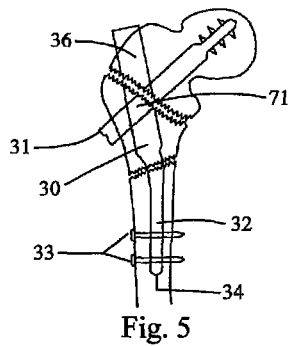
FIG. 5 shows schematic of short length Gamma Nail Implant, implanted in proximal femur bone.
Figures 6, 7:
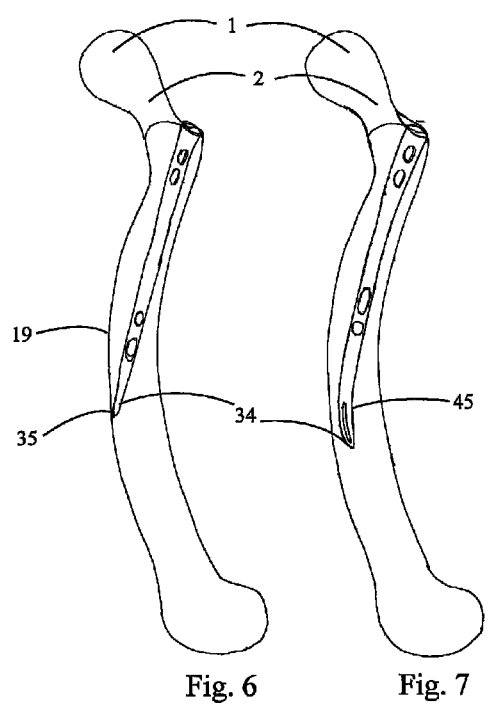
FIG. 6 shows schematic of side view of short length nail of prior art implanted in proximal femur bone showing tip of straight distal end of nail abutting anterior cortex of femur causing stress concentration and pointing effect.
FIG. 7 shows schematic of side view of short length version of nail of invention implanted in proximal femur bone showing curved distal end of nail not abutting anterior cortex of femur.
Figure 28:
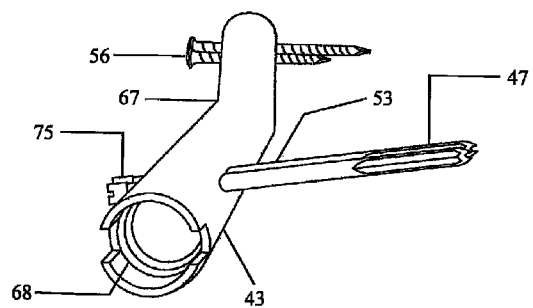
FIG. 28 shows implant assembly of present invention showing connection details of intramedullary nail, sliding proximal hip pins and distal locking screw in perspective view.
Figure 29:
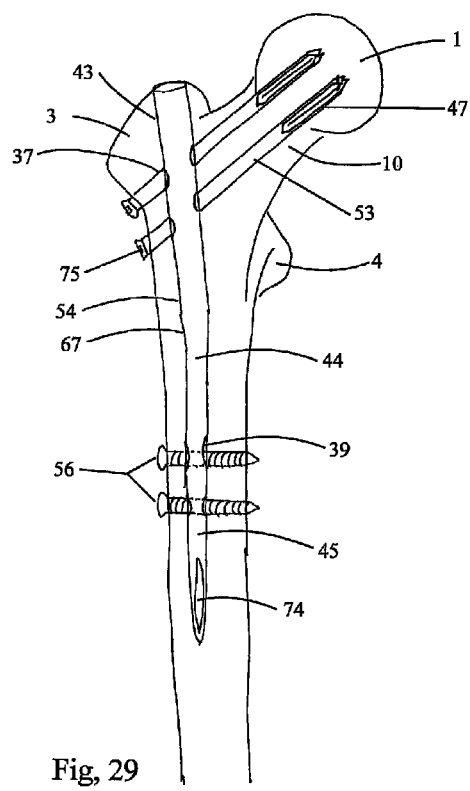
FIG. 29 shows implant assembly of present invention implanted in normal intact human femur showing short length version of intramedullary nail, proximal sliding hip pins and distal interlocking screws.

Referring to FIGS. 12 and 13, Intramedullary nail (42) is cannulated in whole length and comprises of mainly three portions, thigh end portion or head (43) with larger cross section area, intermediate portion or shaft (44) with lesser cross section area than thigh end portion (43) and knee end portion or tail (45) with least cross section area of intramedullary nail (42). The wall thickness of intramedullary nail is also reducing gradually from thigh end (43) to knee end (45). The reason behind providing reducing cross section area and wall thickness of intramedullary nail (42), when moving from thigh end (43) to knee end (45) is to match the implant shape with the shape of the intramedullary canal (17) of femur and to match cortical thickness of femur, which avoids high hoop stress in medullary canal leading to shattering of Greater Trochanter (3), while inserting intramedullary nail (42) in medullary canal (17). This also avoids weakening of bone due to stress shielding effect post operatively. Thigh end (43) of intramedullary nail (42) has relatively smaller diameter which minimize the reaming of bone and removal of bone, thus preserves more biological tissue required for healing of fracture. Referring FIGS. 27 and 28, thigh end(43) of intramedullary nail(42) makes an angle of 5° to 9° with intermediate or shaft part (44) of nail which is known as "mediolateral angle" (67). This angle allows surgeon to have entry point of nail at tip of greater trochanter (3), which is relatively easier. Referring FIGS. 27 and 28, thigh end (43) of intramedullary nail has cannulated internally threaded part (68) to adopt connecting end (59) of targeting device(41) with cannulated connecting bolt(58), Thigh end (43) is provided with plurality of parallel proximal holes(37) for cannulated sliding parallel proximal hip pins(46). To match with the anatomic profile of the femur, the axis of the proximal holes (37) of intramedullary nail (42) makes an angle of about 120° to 140° to match neck shaft angle (13) of femur and the plane of the proximal holes (37) of intramedullary nail (42) makes an angle of about 5° to 20° with the horizontal plane of centre of shaft of femur (14) to match ante version angle of femur (16). Distance between tip of thigh end (43) of intramedullary nail(42) and proximal holes (37) of intramedullary nail(42) is kept at "X1" value, at same time the distance in between proximal holes(37) of intramedullary nail (42) is kept at"Y1" value. The values of "X1" and "Y1" are kept in millimeters such a way that placement of inferior sliding hip pin(61) comes near calcar(10) which contains dense good quality of bone for better fixation and placement of superior proximal sliding hip pin(62) is avoided near superior surface of neck of femur(9) which contains relatively less dense bone. This avoids superior cut through of proximal sliding hip pins from neck and head. Shape of proximal holes (37) of intramedullary nail (42) is kept matching with smooth sliding part (53) of proximal hip pins (46). Referring FIG. 10-13, shapes of proximal holes(37) of intramedullary nail(42) like, "hexagonal" (69) or "key hole" (70) or other than round which gives better rotation stability between proximal holes(37) of intramedullary nail(42) acting as barrel and sliding part(53) of proximal hip pins(46) are preferable to have rotational stability in between two parts of implant. This helps in limited controlled guided collapse of fracture avoiding malunion of fracture. Diameter of plural proximal holes (37) of intramedullary nail (42) is relatively smaller. Plurality of relatively smaller diameter proximal holes (37) of intramedullary nail (42) reduces chances of brakeage of nail on weight bearing in comparison to single large diameter proximal hole (71) in prior art intramedullary nail as shown in FIG. 5. Intermediate or shaft part (44) of nail differs in short length version (54) and full length version (55) of intramedullary nails (42). In full length version (55) intramedullary nail, the intermediate part has anterior curvature to match the anterior curvature (18) of femur, but do not have holes for distal interlocking screws.

In short length version (54) nail intermediate portion (44) of intramedullary nail (42) is straight and has plurality of distal locking holes (39) to match with plurality of distal holes (40) of targeting device (41). Distance between tip of thigh end (43) of short length version (54) intramedullary nail (42) and distal holes (39) of intramedullary nail is kept at "Z1" value. Value of "Z1" is kept in millimeters such that distal holes (39) of intramedullary nail matches with distal holes (40) of targeting device. This makes sure distal interlocking of screws through targeting device (41) in short length version (54) intramedullary nails without any chance to miss the target due to anterior curvature (18) of shaft of femur. This helps surgeon to avoid harmful fluoroscopic radiation exposure. Depending upon their cross section, either oval or round they are called distal dynamic hole (72) and distal static hole (73) respectively, as known to person skilled in art. As shown in FIGS. 12 and 13, the short length version (54) and full length version (55) of nails have different sequence of distal dynamic hole (72) and distal static hole (73). Distal dynamic holes provide limited vertical collapsibility of fracture on weight bearing by patient as known to person skilled in art. Knee end (45) of intramedullary nail (42) has grooves (74) which gives it flexibility avoiding stress rising at knee end (45). Knee or distal part (45) of short length version (54) intramedullary nail (42) has anterior curvature to match anterior curvature (18) of shaft (5) of femur. This avoids stress rising and "pointing effect" (35) by tip(34) of knee end(45) of intramedullary nail(42) and thus prevents postoperative thigh pain to patients and complication of fracture of shaft of femur beneath tip(34) of nail later on. Intramedullary Nails (42) are of right and left side for different side of femur fractures due to its complete anatomical profile like femur bone.

Referring to FIG. 15-19, proximal sliding hip pin (46) which is cannulated in its whole length which helps surgeon for precise placement in neck (2) and head (1) part of femur guided by short sharp guide pin (64), Diameter of these parallel sliding proximal hip pins (46) is relatively smaller, which requires less reaming and removal of bone from neck (2) and head (1) part of femur. Proximal hip pin (46) comprises mainly of three parts namely head part (75), gliding smooth shaft part (53) and triflanged part (47) holding neck and head of femur. Head part (75) has larger diameter than shaft part (53) which does not sink in intact lateral cortex (22) of femur and prevents inadvertent push of hip pin in hip joint. This also helps in impaction of fracture gap. Gliding smooth shaft part (53) has outer shape in cross section matching inner shape of proximal holes (37) in intramedullary nail (42). Referring FIGS. 17 and 18 shapes like "Hexagonal" (76) or "Key shape" (77) or shapes other than round is preferable to have better rotational stability in between two parts of implant for limited guided controlled collapse of fracture avoiding malunion of fracture. As shown in FIGS. 15, 16 and 19 triflanged part (47) has scalloped three flat equal surfaces up to 15 mm to 50 mm of span with more taper to have better grip and rotational stability of proximal fragment of neck(2) and head(1) of femur particularly in osteoporotic bone. As shown in FIG. 19 Triflanged part (47) has three scalloped relatively flat equal surfaces with central cannulation (78). As shown in FIGS. 29-34, one of the flat surface of triflange part (47) of inferior sliding proximal hip pin (61) gives better rotation stability due to well fit in flat part of calcar(10) of neck(2). As shown in FIG. 29-34 one of the flat surfaces of triflange part (47) of superior sliding proximal hip pin (62) prevents cut through from superior surface of neck due to its flatness. Due to triflange design, method of its insertion is by gentle hammering which does not remove bone from head and neck part of femur like thread design, but it compacts bone, thus preserving bone tissue. Other than thread design like "u" profile or "diamond" shape is also preferable to have same advantages. As shown in FIG. 16, triflanged part(47) has optional multiple small holes(48) of at least 2 mm diameter connecting to main cannulation to inject liquid bone cement or other augmentation material(49) to augment the fixation in head and neck part of femur in severely osteoporotic bone. The purpose of providing plurality of parallel proximal sliding hip pins (46) is to achieve better rotational stability of fractured proximal fragment of femur.

FIG. 20 shows distal locking screw (56) which is a conventional locking self tapping screw known to person skilled in art. It prevents rotation of femur on intramedullary nail providing good hold in distal fragment. The purpose of providing plurality of distal locking screw (56) is to achieve better rotational stability of fractured distal fragment of femur.

Figures 26, 27:
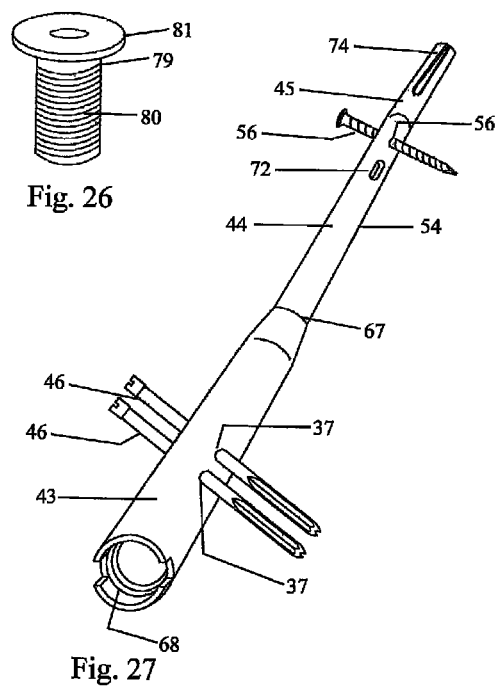
FIG. 26 shows elevation of end cap. 25
FIG. 27 shows implant assembly of present invention showing connection details of intramedullary nail, sliding proximal hip pins and distal locking screw.

FIG. 26 shows cannulated end cap (79), which has threaded part (80) to match with internally threaded part of thigh end (43) of intramedullary nail and head part (81) with larger diameter than threaded part (80), but equal diameter to thigh end (43) of intramedullary nail. Threaded part (80) is used to seal the internally threaded part of thigh end (43) of intramedullary nail. This avoids tissue ingrowths in threaded part of thigh end (43) intramedullary nail (42) and helps to remove intramedullary nail easily later on. Head part (81) has variable length from 5 mm to 25 mm. In certain circumstances surgeon has to push more intramedullary nail (42) inside the medullary canal (17) for precise placement of proximal hip pins (46) in neck (2) and head (1) part of femur. In such circumstances, variable length of cannulated end caps (79) allows to extend the length of intramedullary nail (42) accordingly up to tip of greater trochanter(3). This enhances the fixation of intramedullary nail (42) and makes access of internally threaded part of thigh end (43) of intramedullary nail easy at the time of removal of intramedullary of nail. As shown in FIGS. 14, 15, and 16, optional washer (57) is of at least 1 mm thickness with slit and it has internal diameter matching with outer diameter of shaft or sliding part(53) of proximal hip pin (46) and has outer diameter larger than head part (75) of proximal hip pin (46). This avoids sinking in of head part (75) of proximal hip pin(46), when there is small void or crack in lateral cortex (22) of femur. This also helps impaction of fracture gap and as it prevents sinking in of head part (75) of proximal hip pin (46) and thus does not obstruct collapse of fracture.

Figure 30:
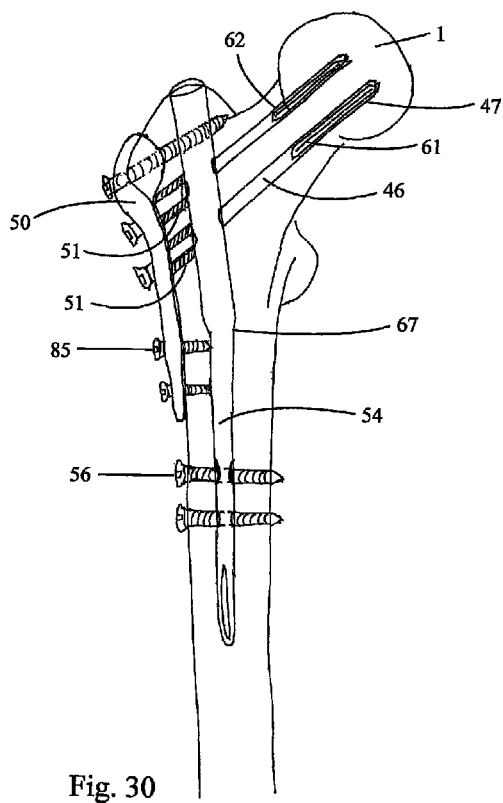
FIG. 30 shows implant assembly of present invention implanted in normal intact human femur showing short length version of intramedullary nail, proximal sliding hip pins, distal interlocking screws and buttress plate with barrels supporting lateral cortex of femur.

As shown in FIGS. 21 and 30, optional barrels (51) are cylindrical tubes having at least 1 mm thickness, oblique at ends, inner diameter and shape is matching with the outer diameter and outer shape of sliding shaft part (53) of proximal smooth pins (46). One end of tube may have rim to fit on central large oblong hole (52) of the buttress plate (50). These barrels are used with or without buttress plate (50) when there is badly broken lateral cortex (22) of shaft of femur. This helps to provide uniform gliding surface for limited controlled gliding of proximal hip pins (46) leading to collapse of fracture and healing of fracture on weight bearing by patient.

Figures 24, 25:
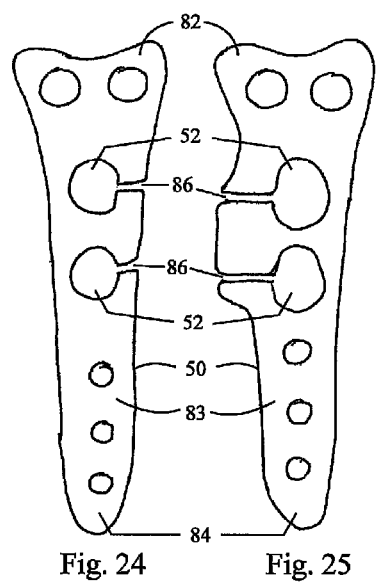
FIGS. 24 and 25 show elevation of buttress plates of alternate design.

As shown in FIGS. 24, 25 and 30, optional buttress plate (50) is of at least 2 mm thickness, curved, broad, contourable, matching the shape of lower part of greater trochanter (3) and lateral cortex (22) of shaft of femur comprising short transverse upper part (82) and lower long vertical part (83). Upper transverse part (82) is curved having at least two holes for its fastening by screws with greater trochanter (3). Lower long vertical part (83) has reducing transverse diameter from proximal to distal part having narrow obtuse end (84). Purpose of narrow obtuse end(84) is for easy sliding of buttress plate(50) on lateral cortex(22) of femur from small incision made for entry of intramedullary nail(42) from tip of greater trochanter(3). Lower long vertical part (83) of buttress plate (50) has at least two central large holes (52) for proximal sliding hip pins and at least two small holes in lower part for cortical screws (85). Shape and diameter of central large holes (52) are matching with the outer shape and diameter of sliding smooth shaft part (53) of proximal hip pins (46). Central large holes have slit (86) on one of the border of at least 2 millimeter for easy positioning of buttress plate (50) on guide pin (64). In cases where fracture pattern is such that, there is void or comminution in lateral cortex (22) of femur, this buttress plate (50) is used as shown in FIG. 30. This provides lateral buttress support and side platform to proximal fragment and helps to maintain anatomic reduction and prevents uncontrolled unwanted collapse of fracture and prevents inadvertent migration of hip pins in hip joint leading to pain, shortening of limb and limp to patient.

Stainless steel or titanium is preferred materials for the implant.

BEST MODE OF INVENTION

Figure 34:
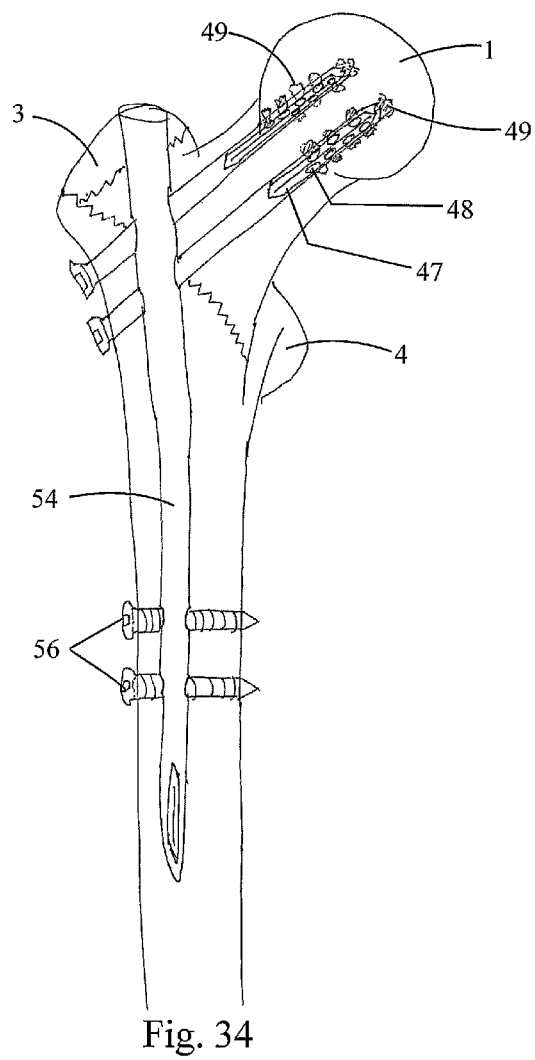
FIG. 34 shows implant assembly of present invention implanted in human femur having fractures in proximal femur with osteoporotic bone showing short length version of intramedullary nail, proximal sliding hip pins with multiple holes, augmentation material like liquid bone cement came out of these multiple holes in head and neck of femur and distal interlocking screws.

In case of proximal femur fracture the proposed implant is implemented in the manner given below:

First of all patient is positioned on fracture table and anatomical reduction of proximal femur fractures and fracture of shaft, if associated with it, is done and confirmed with imaging device in both planes known to those ordinarily skilled in art. Local parts are prepared and draped to get sterile field as per usual procedure known to person skilled in art. Short length incision is made to expose the tip of greater trochanter (3). With the help of entry tool or cannulated awl an aperture is made at tip of greater trochanter (3) in direction and connecting it to intramedullary canal (17). A long blunt medullary guide pin (63) is passed from this aperture down across the fracture line up to lower part of intramedullary canal (17) and its position is checked with imaging device. With the help of cannulated flexible reamers, appropriate reaming of intramedullary canal is done over this guide pin (63), in a manner known to person skilled in art. After preparation of medullary canal (17), intramedullary nail (42) is mounted on targeting device (41) according to the left or right side with the help of (temporary) cannulated connecting bolt (58). Then mounted intramedullary nail (42) with targeting device (41) is checked outside to ensure the proximal sliding hip pins (46) and distal locking screws (56) are inserted properly inside proximal holes (37) of nail and distal holes of nail (39) respectively. Now the intramedullary nail (42) mounted with targeting device (41) is inserted on guide pin (63) in prepared intramedullary canal (17) by gentle push and rotatory movement with the help of handle part (60) of targeting device (41) in downward direction. Now position of intramedullary nail (42) and position of proximal holes (37) of nail are confirmed with imaging technique. After satisfactory insertion of intramedullary nail, medullary guide pin (63) is removed. As shown in FIG. 31, now set of three telescoping protection sleeves (65) are passed through proximal holes (38) of targeting device (41) and pushed to touch the lateral cortex (22) of femur through small skin incision and incision in fascia lata. Without rotating targeting device(41), sharp short guide pins (64) are passed through pin sleeve from lateral cortex(22) to neck(2) and head(1) part of femur, passing through center of proximal holes(37) of intramedullary nail(42) in position in medullary canal(17), makes an angle of 120° to 140° to central axis of shaft of femur(11) to match neck shaft angle (13) and a the same time making an angle of 5° to 20° with horizontal plane of centre of shaft of femur(14) to match angle of ante version(16). At least two parallel guide pins (64) passed one inferior near dense calcar (10) part of neck and one superior at the centre of neck in anteroposterior plane imaging and in lateral plane imaging both should be in the centre in of neck and head part. Now pin sleeve is removed and cannulated "step drill or step reamer" is used over guide pin through drill sleeve. Step drill or step reamer is containing two diameter: a smaller diameter of span corresponding span and root diameter of the triflanged part of proximal hip pin (46) for better fixation of triflanged part in head and neck of femur; and a larger diameter which is equal to the diameter of the smooth sliding portion (53) of proximal hip pin (46) for easy sliding of proximal hip pin(46) in proximal holes(37) of intramedullary nail(42) leading to post operative compression of fragments on weight bearing by patient. After making appropriate drill hole in head and neck guided on guide pin (64), length of proximal hip pins (46) are measured. Now drill sleeve is removed and measured length proximal hip pin (46) is inserted on guide pin (64) through tissue protection sleeve, by gentle hammering on insertion tool. As gentle hammering is done triflanged part (47) having more taper gets better grip and large diameter head part (75) of proximal hip pin (46) touching the lateral cortex (22) pushes the lateral fragment towards fragment having neck (2) and head (1) part of femur, thus by impaction reduces fracture gap during operation and improves bone to bone contact for better healing. This impaction is done with large diameter head part (75) in cases where lateral cortex (22) of femur is totally intact. In case of small void or crack in lateral cortex (22), optional slit washer (57) can be used to get impaction. As shown in FIG. 30, in cases where there is comminution in lateral cortex (22) or it is badly broken, optional buttress plate (50) with or without barrels (51) is used. Optional buttress plate (50) is first contoured to match the shape of lateral cortex (22) of greater trochanter (3) and shaft (5) of femur. Narrow obtuse end (84) is glided on lateral cortex (22) under the muscles downward from small incision made for entry of intramedullary nail (42), and central large holes (52) in buttress plate (50) are positioned on guide pins (64) through slit (86) in these holes. Now optional barrels (51) are passed through the central large holes of plate. Now proximal hip pins are passed through these barrels (51)

having internal surface matching with outer surface of sliding part (53) of proximal hip pins (46). Now gentle hammering on head part (75) of hip pin passing through buttress plate (50) allows impaction of fracture, as the buttress plate (50) supports broken lateral cortex (22) well. Now through distal holes of buttress plate (50) fastening cortical screws (85) are applied to lateral cortex (22) of femur. Upper transverse part (82) of buttress plate (50) is fastened with greater trochanter (3), by screws or any other anchoring device, known to person skilled in art. In cases where femur bone is osteoporotic, triflange proximal hip pins with multiple holes is used to get augmentation of fixation as shown in FIG. 34. After insertion of proximal sliding hip pins (46) with multiple holes (48), liquid bone cement or other augmentation material (49) is injected to central cannulation (78) of proximal hip pins by suitable syringe like apparatus. As multiple holes (48) in triflange part (47) is connected to central cannulation (78), augmentation material (49) will pour out in head (1) and neck and head(1) part of femur making bondage to give better fixation. In case of short length version (54) of intramedullary nail, distal locking screws (56) are passed through distal block of holes (40) in targeting device without the fluoroscopic radiation exposure to surgeon. As shown in FIG. 31 set of two telescoping sleeves (66) passed through distal holes (40) of targeting device (41) are pushed, touching the lateral cortex (22) of shaft (5) of femur, through small skin incision and small cut in fascia lata. Drill hole is made with solid drill bit passing through drill sleeve from lateral cortex (22), through distal holes (39) in the nail and then making hole in medial cortex (21). Measured length distal interlocking screws (56) are passed to give desired rotational stability. In case of full length version (55) of intramedullary nail, distal locking is done with the help of fluoroscopy by "free hand method "known to person skilled in art. After final fixation targeting device (41) is disconnected by unscrewing connecting bolt (58). Now cannulated end cap (79) of suitable length is threaded to internally threaded part of thigh end (43) of intramedullary nail (42) to seal it. Now small skin incisions are closed in layers and dressing is applied.

Postoperatively patients are allowed to have pain oriented weight bearing. Initially implant takes full load of different forces acting on femur and it reacts effectively by allowing limited controlled collapse of fracture gap by sliding of proximal hip pins (46), leading to early bone to bone contact and healing. In this way, gradually the implant diverts the above said load to fractured femur bone stimulating healing of femur bone without any post operative setbacks.

Those of ordinary skill in the art will further understand and appreciate from the totality of the foregoing disclosure, that the various alternative features and components shown and discussed in conjunction with FIG. 1 through 34, may be practiced in accordance with various installation and withdrawal methodologies, all of which combinations are intended to come within the spirit and the scope of the present invention, without rediscussion thereof. Such alternative methodologies are intended to include the use of different intramedullary nail embodiments practiced in accordance with the invention. It should be further understood by those of ordinary skill in the art that the foregoing presently preferred embodiments are exemplary only, and that the attendant description thereof is likewise by way of words of example rather than words of limitation, and their use does not preclude inclusion of such modifications, variations, and/or additions to the present invention (either apparatus or methodology) as would be readily apparent to one of ordinary skill in the art, the scope of the present invention being set forth in the appended claims.

INDUSTRIAL APPLICABILITY

An implant assembly for proximal femur fracture of the present invention is biomechanically a superior method of treating a wide range of femoral fracture patterns, such as a wide range of femoral fracture patterns, such as combination neck/shaft fractures, any type of femoral neck fracture, intertrochanteric fractures, subtrochanteric fractures, severely comminuted shaft fractures, reconstruction of the femoral shaft, allograft reconstruction of the femoral shaft after tumor resection, and leg lengthening. Other uses will be recognized by those skilled in the art.

What is claimed is:

1. An implant assembly for treating proximal femur fractures and same side fractures of a shaft of a femur, including:
   A) a one piece intramedullary nail comprising
      a first plurality of proximal holes and a first plurality of distal holes,
   B) a targeting device connectable to said intramedullary nail comprising
      a second plurality of proximal holes and a second plurality of distal holes, wherein said second plurality of distal holes are placed offset vertically at a distance $d_1 > 0$ in relation to the second plurality of proximal holes,
   a) wherein each of said first plurality of proximal holes defining a proximal centerline extending through a center of corresponding second plurality of proximal holes of said targeting device and extendable through a midsection of a head portion and a neck portion of said femur, said proximal centerline intersects with a longitudinal axis of said intramedullary nail defining a first plane of center for of each of said first plurality of proximal holes,
   b) wherein each of said first plurality of distal holes defining a distal centerline extending through a center of corresponding second plurality of distal holes of said targeting device and extendable through a midsection of said shaft of said femur, said distal centerline intersects substantially perpendicular with the longitudinal axis of said intramedullary nail defining a second plane of center for each of said first plurality of distal holes and;
   c) wherein said first plane of center for each of first plurality of proximal holes intersects at an angle $a_1$ with said second plane of center for each of first plurality of distal holes substantially all along the longitudinal axis,
   C) a buttress plate comprising a plurality of central large holes and a plurality of small holes wherein at least one of said plurality of central large holes is characterized having a slit of at least 2 millimeter, and;
   a plurality of barrels.

2. An implant assembly of claim 1 further comprising a plurality of proximal sliding hip pins, each of said plurality of proximal hip pins comprises a head part, a smooth part capable of sliding within said first plurality of proximal holes of said intramedullary nail; and a triflanged part with scalloped three flat equal surfaces up to 15 mm to 50 mm of span, said triflanged part is characterized having a gradual taper towards a leading end.

3. An implant assembly of claim 2 wherein said triflanged part is characterized having a plurality of holes of at least 2 mm diameter connecting a central cannulation of said proximal hip pin to allow injection of liquid cement or other augmentation material to augment the engagement of said triflanged part of said proximal hip pin in said head portion and said neck portion of said femur without hampering sliding of said smooth part within said first plurality of proximal holes of said intramedullary nail.

4. An implant assembly of claim 2, wherein said smooth part of at least one of said plurality of proximal hip pins has a shape other than round.

5. An implant assembly of claim 1, wherein said intramedullary nail has a central cannulation.

6. An implant assembly of claim 1, wherein said buttress plate has a narrow obtuse end.

7. An implant assembly of claim 1, wherein said intramedullary nail has an anterior curvature.

8. An implant assembly of claim 1, wherein a connecting end of said targeting device is short and compact.

9. An implant assembly of claim 1, wherein at least one of said first plurality of proximal holes has a shape other than round.

10. A method of treating a fracture located between a head of a femur bone and a medullary canal of the femur utilizing a buttress plate having a plurality of central large holes and a plurality of small holes wherein at least one of said plurality of central large holes is characterized having a slit of at least 2 millimeter with a plurality of barrels in combination with a one piece intramedullary nail connectable to a targeting device, said method comprising the steps of:
   a) making a first minimal incision and a first aperture at a greater trochanter to connect to the medullary canal of the femur bone;
   b) inserting from said first aperture said intramedullary nail into the medullary canal, said intramedullary nail comprising:
      1) a first plurality of proximal holes each defining a proximal centerline extending through a center of corresponding second plurality of proximal holes of said targeting device and extendable through a midsection of a head portion and a neck portion of the femur, said proximal centerline intersects with a longitudinal axis of said intramedullary nail to define a first plane of center for each of said first plurality of proximal holes,
      2) a first plurality of distal holes each defining a distal centerline extending through a center of corresponding second plurality of distal holes of said targeting device and extendable through a midsection of a shaft of the femur, said distal centerline intersects substantially perpendicular with the longitudinal axis of said intramedullary nail to define a second plane of center for each of said first plurality of distal holes and;
      3) wherein said second plurality of distal holes are placed offset vertically at a distance $d_1 > 0$ in relation to the second plurality of proximal holes, said first plane of center for each of first plurality of proximal holes intersects at an angle $a_1$ with said second plane of center for each of first plurality of distal holes substantially all along the longitudinal axis;
   c) making a second minimal incision and a plurality of drill holes in a lateral cortex of said femur to target each of said first plurality of proximal holes and said midsection of said head and said neck wherein said drill holes are made by using a step drill bit or a step reamer that is guided by a plurality of sharp short guide pins;
   d) sliding a narrow obtuse end of said buttress plate on a surface of said greater trochanter and said lateral cortex through said first minimal incision such that the plurality of central large holes of said buttress plate rests on said plurality of sharp short guide pins through the slit in said plurality of central large holes;
   e) positioning said plurality of barrels in said plurality of central large holes guided by said plurality of short sharp guide pins;
   f) inserting, by gentle hammering, proximal hip pins through corresponding one of said central large holes and one of said first plurality of proximal holes such that said proximal hip pins are extendable across the fracture and slidably and firmly engagable into the said neck portion and said head portion of said femur and capable of impaction of said fracture.

11. The method of claim 10 further comprising steps of: inserting at least one of plurality of distal locking screws engagable to said lateral cortex and a medial cortex of said femur bone through one of plurality of said small holes of said buttress plate and one of the said first plurality of distal holes of said intramedullary nail.

12. An implant assembly to treat fractures of the femur bone comprising:
   A) a buttress plate having a plurality of central large holes and a plurality of small holes wherein at least one of said plurality of central large holes is characterized having a slit of at least 2 millimeter,
   B) a one piece intramedullary nail connectable to a targeting device comprising
      a first plurality of proximal holes and a first plurality of distal holes,
      a second plurality of proximal holes and a second plurality of distal holes of said targeting device, wherein said second plurality of distal holes are placed offset vertically at a distance $d_1 > 0$ in relation to the second plurality of proximal holes,
      a) wherein each of said first plurality of proximal holes defining a proximal centerline extending through a center of corresponding second plurality of proximal holes of said targeting device and extendable through a midsection of a head portion and a neck portion of the femur, said proximal centerline intersects with a longitudinal axis of said intramedullary nail defining a first plane of center for each of said first plurality of proximal holes,
      b) wherein each of said first plurality of distal holes defining a distal centerline extending through a center of corresponding second plurality of distal holes of said targeting device and extendable through a midsection of the shaft of the femur, said distal centerline intersects substantially perpendicular with the longitudinal axis of said intramedullary nail defining a second plane of center for each of said first plurality of distal holes,
      c) wherein said first plane of center for each of first plurality of proximal holes intersects at an angle $a_1$ with said second plane of center for each of first plurality of distal holes substantially all along the longitudinal axis and;
   C) a plurality of barrels.

13. An implant assembly of claim 12 further comprising a plurality of proximal sliding hip pin, each of said plurality of proximal hip pins comprises a head part, a smooth part capable of sliding within said first plurality of proximal holes of said intramedullary nail; and a triflanged part with scalloped three flat equal surfaces up to 15 mm to 50 mm of span, said triflanged part is characterized having a gradual taper towards a leading end.

14. An implant assembly of claim 13, wherein said triflanged part is characterized having a plurality of holes of at least 2 mm diameter connecting a central cannulation of said proximal hip pin to allow injection of liquid cement or other augmentation material to augment the engagement of said triflanged part of said proximal hip pin in said head portion and said neck portion of said femur without hampering sliding of said smooth part within said first plurality of proximal holes of said intramedullary nail.

15. An implant assembly of claim 13, wherein said smooth part of at least one of said plurality of proximal hip pins has is a shape other than round.

16. An implant assembly of claim 12, wherein said intramedullary nail has an anterior curvature.

17. An implant assembly of claim 12, wherein at least one of said first plurality of proximal holes has a shape other than round.

18. An implant assembly of claim 12, wherein said buttress plate has a narrow obtuse end.

\* \* \* \* \*